United States Patent
Costello (10) Patent No.: US 9,974,677 B2
(45) Date of Patent: May 22, 2018

(54) WIRE COLLECTION DEVICE FOR STENT DELIVERY SYSTEM

(71) Applicant: Cook Medical Technologies LLC, Bloomington, IN (US)

(72) Inventor: Kieran Costello, Ballina/Killaloe (IE)

(73) Assignee: Cook Medical Technologies LLC, Bloomington, IN (US)

( * ) Notice: Subject to any disclaimer, the term of this patent is extended or adjusted under 35 U.S.C. 154(b) by 752 days.

(21) Appl. No.: 14/461,041

(22) Filed: Aug. 15, 2014

(65) Prior Publication Data

US 2015/0057739 A1 Feb. 26, 2015

Related U.S. Application Data

(60) Provisional application No. 61/867,926, filed on Aug. 20, 2013.

(51) Int. Cl.
| | |
|---|---|
| *A61F 2/06* | (2013.01) |
| *A61F 2/966* | (2013.01) |
| *A61F 2/962* | (2013.01) |
| *A61F 2/95* | (2013.01) |

(52) U.S. Cl.
CPC .............. *A61F 2/966* (2013.01); *A61F 2/95* (2013.01); *A61F 2/962* (2013.01); *A61F 2002/9517* (2013.01); *A61F 2002/9665* (2013.01)

(58) Field of Classification Search
CPC .. A61F 2/95; A61F 2/962; A61F 2/966; A61F 2002/9517; A61F 2002/9665
See application file for complete search history.

(56) References Cited

U.S. PATENT DOCUMENTS

| | | |
|---|---|---|
| 706,606 A | 8/1902 | Spriggs |
| 844,550 A | 2/1907 | Thomasson |
| 1,615,534 A | 1/1927 | Cassel |
| 2,939,680 A | 6/1960 | Powell |
| 3,589,486 A | 6/1971 | Kelch |
| 4,466,576 A | 8/1984 | Simson |
| 4,483,326 A | 11/1984 | Yamaka et al. |
| 5,026,377 A | 6/1991 | Burton et al. |

(Continued)

FOREIGN PATENT DOCUMENTS

| | | |
|---|---|---|
| EP | 1 251 796 B1 | 12/2004 |
| EP | 2431009 | 3/2012 |

(Continued)

OTHER PUBLICATIONS

Abbott Laboratories, "Absolute Pro® .035 Biliary Self-Expanding Stent System," obtained at internet address <http://www.abbotvascular.com/docs/ifu/peripheral_intervention/eIFU_absolute_pro_35_Biliary_SelfExpanding_Stent_System.pdf>, EL2070955, dated Jul. 24, 2009, 11 pages.

*Primary Examiner* — Robert Lynch
(74) *Attorney, Agent, or Firm* — Brinks Gilson & Lione (57) ABSTRACT

A wire collection device for a stent delivery system includes a plurality of nested wire collection drums with a first drum concentric in a second drum. A thumbwheel coupled to the first drum can rotate to actuate rotation of the first drum to collect the retraction wire around the diameter of the first drum. A catching mechanism can rotate about the first drum to engage a catch portion of the second drum and actuate rotation of the second drum to collect the retraction wire around the outer diameter of the second drum. This increases the collection diameter of the retraction wire to provide a mechanical advantage for sheath retraction.

13 Claims, 10 Drawing Sheets

(56) References Cited

U.S. PATENT DOCUMENTS

| | | |
|---|---|---|
| 5,088,581 A | 2/1992 | Duve |
| 5,534,007 A | 7/1996 | St. Germain et al. |
| 5,772,669 A | 6/1998 | Vrba |
| 5,904,667 A | 5/1999 | Falwell |
| 5,968,052 A | 10/1999 | Sullivan, III et al. |
| 6,059,813 A | 5/2000 | Vrba et al. |
| 6,190,360 B1 | 2/2001 | Iancea et al. |
| 6,238,402 B1 | 5/2001 | Sullivan, III et al. |
| 6,273,895 B1 | 8/2001 | Pinchuk et al. |
| 6,387,977 B1 | 5/2002 | Sawhney et al. |
| 6,395,017 B1 | 5/2002 | Dwyer et al. |
| 6,520,983 B1 | 2/2003 | Colgan et al. |
| 6,607,551 B1 | 8/2003 | Sullivan et al. |
| 6,660,031 B2 | 12/2003 | Tran et al. |
| 6,773,446 B1 | 8/2004 | Dwyer et al. |
| 6,805,314 B2 | 10/2004 | Hopper |
| 6,860,898 B2 | 3/2005 | Stack et al. |
| 6,884,259 B2 | 4/2005 | Tran et al. |
| 6,905,461 B2 | 6/2005 | Hino |
| 6,939,352 B2 | 9/2005 | Buzzard et al. |
| 7,052,511 B2 | 5/2006 | Weldon et al. |
| 7,122,050 B2 | 10/2006 | Randall et al. |
| 7,300,438 B2 | 11/2007 | Falwell et al. |
| 7,300,456 B2 | 11/2007 | Andreas et al. |
| 7,604,611 B2 | 10/2009 | Falwell et al. |
| 7,615,042 B2 | 11/2009 | Beyar et al. |
| 7,674,282 B2 | 3/2010 | Wu et al. |
| 7,758,625 B2 | 7/2010 | Wu et al. |
| 7,815,669 B2 | 10/2010 | Matsuoka et al. |
| 7,935,141 B2 | 5/2011 | Randall et al. |
| 7,967,829 B2 | 6/2011 | Gunderson et al. |
| 7,976,574 B2 | 7/2011 | Papp |
| 7,993,384 B2 | 8/2011 | Wu et al. |
| 8,025,692 B2 | 9/2011 | Feeser |
| 8,075,606 B2 | 12/2011 | Dorn |
| 8,216,296 B2 | 7/2012 | Wu et al. |
| 8,323,326 B2 | 12/2012 | Dorn et al. |
| 8,337,077 B2 | 12/2012 | Giacobino |
| 8,500,789 B2 | 8/2013 | Wuebbeling et al. |
| 2003/0163085 A1 | 8/2003 | Tanner et al. |
| 2004/0006380 A1 | 1/2004 | Buck et al. |
| 2004/0087979 A1 | 5/2004 | Field |
| 2005/0033403 A1 | 2/2005 | Ward et al. |
| 2005/0149159 A1 | 7/2005 | Andreas et al. |
| 2005/0256452 A1 | 11/2005 | DeMarchi et al. |
| 2005/0256562 A1 | 11/2005 | Clerc et al. |
| 2005/0273151 A1 | 12/2005 | Fulkerson et al. |
| 2006/0259124 A1 | 11/2006 | Matsuoka et al. |
| 2007/0032860 A1 | 2/2007 | Brooks et al. |
| 2007/0055340 A1 | 3/2007 | Pryor |
| 2007/0055342 A1 | 3/2007 | Wu et al. |
| 2007/0088421 A1 | 4/2007 | Loewen |
| 2007/0156225 A1 | 7/2007 | George et al. |
| 2007/0168014 A1 | 7/2007 | Jimenez et al. |
| 2007/0191925 A1 | 8/2007 | Dorn |
| 2007/0219617 A1 | 9/2007 | Saint |
| 2008/0091257 A1 | 4/2008 | Andreas et al. |
| 2008/0188920 A1 | 8/2008 | Moberg et al. |
| 2008/0300574 A1 | 12/2008 | Belson et al. |
| 2008/0319387 A1 | 12/2008 | Amisar et al. |
| 2009/0024133 A1 | 1/2009 | Keady et al. |
| 2009/0099641 A1 | 4/2009 | Wu et al. |
| 2009/0125093 A1 | 5/2009 | Hansen |
| 2009/0210046 A1 | 8/2009 | Shumer et al. |
| 2009/0270969 A1 | 10/2009 | Fargahi et al. |
| 2010/0004606 A1 | 1/2010 | Hansen et al. |
| 2010/0049297 A1 | 2/2010 | Dorn |
| 2010/0076541 A1 | 3/2010 | Kumoyama |
| 2010/0137967 A1 | 6/2010 | Atlani et al. |
| 2010/0145431 A1 | 6/2010 | Wu et al. |
| 2010/0168834 A1 | 7/2010 | Ryan et al. |
| 2010/0174290 A1 | 7/2010 | Wüebbeling et al. |
| 2011/0295354 A1 | 12/2011 | Bueche et al. |
| 2012/0022635 A1 | 1/2012 | Yamashita |
| 2012/0041537 A1 | 2/2012 | Parker et al. |
| 2012/0059448 A1 | 3/2012 | Parker et al. |
| 2012/0101562 A1 | 4/2012 | Gunderson et al. |
| 2012/0123516 A1 | 5/2012 | Gerdts et al. |
| 2012/0143304 A1 | 6/2012 | Wübbeling et al. |
| 2012/0158117 A1 | 6/2012 | Ryan |
| 2012/0158120 A1 | 6/2012 | Hacker et al. |
| 2012/0296409 A1 | 11/2012 | Kawakita |
| 2012/0330401 A1 | 12/2012 | Sugimoto et al. |
| 2013/0013047 A1 | 1/2013 | Ramos et al. |
| 2013/0018451 A1 | 1/2013 | Grabowski et al. |
| 2013/0110223 A1 | 5/2013 | Munsinger et al. |
| 2014/0188209 A1 | 7/2014 | Loewen |
| 2015/0297378 A1 | 10/2015 | Senness |

FOREIGN PATENT DOCUMENTS

| | | |
|---|---|---|
| WO | WO 94/16762 A1 | 8/1994 |
| WO | WO 2007/044929 A1 | 4/2004 |
| WO | WO 2006/014233 A2 | 2/2006 |
| WO | WO 2007/022395 A1 | 2/2007 |
| WO | WO 2008/034793 A1 | 3/2008 |
| WO | WO 2008034793 | 3/2008 |
| WO | WO 2008/124844 A1 | 10/2008 |
| WO | WO 2008/134104 A2 | 11/2008 |
| WO | WO 2010/120671 A1 | 10/2010 |

SECTION A-A
FIG. 2

SECTION B-B
FIG. 7

SECTION C-C
FIG. 10

WIRE COLLECTION DEVICE FOR STENT DELIVERY SYSTEM

CROSS-REFERENCE TO RELATED APPLICATIONS

This application is a non-provisional application which claims priority to U.S. provisional application Ser. No. 61/867,926, filed Aug. 20, 2013, which is incorporated by reference herein in its entirety.

TECHNICAL FIELD

Embodiments disclosed in the present application relate generally to wire collection devices for providing a mechanical advantage in a stent delivery system.

BACKGROUND

Current delivery systems for self-expanding stents generally employ "pin and pull" systems that include an inner catheter extending through an outer sheath. Typically, the stent is placed inside the outer sheath and held in a compressed position by the outer sheath as the outer sheath and inner catheter are inserted into a patient's body vessel. To deploy the stent, the user retracts, or pulls, the outer sheath using one hand while the other hand holds the inner catheter stationary to maintain position of the stent as the outer sheath is retracted, thereby allowing the stent to gradually expand as the outer sheath uncovers the stent.

In these "pin and pull" systems, the user has difficulty maintaining the position of the inner catheter while pulling on the outer sheath because of resistance between the inner catheter and outer sheath, between the outer sheath and the stent, and between the outer sheath and the surrounding vascular walls, or other surrounding blood vessel or body vessel. To overcome this resistance the user may need to exert a large amount of force that leads to various complications, including for example, inaccurate stent positioning, displacement of the stent, shortening or lengthening of the stent, or other damage to the structure of the stent, or damage to the target vessel.

"Pin and pull" systems may also have other disadvantages, including, for example, lack of control during stent deployment and requirement of assistance from a second person. The resistance between the outer sheath and stent varies as more of the stent is uncovered and the stent expands. Specifically, the stent's self-expanding outward circumferential bias frictionally binds it against the outer sheath. During sheath retraction, this binding force decreases as the stent is released, which correspondingly decreases the retraction force needed on the outer sheath. Thus, stent deployment is difficult to control because the required deployment force varies as the outer sheath retracts across the surface of the stent. As a result, the user must vary the force applied to the outer sheath and the inner sheath in order to maintain a steady deployment speed and ensure accurate stent placement. In most pin and pull systems, the ratio of handle movement to stent deployment distance is 1:1, requiring the user to move faster to deploy longer stents and increasing difficulty in controlling the stent. Because the user's hands are holding the distal ends of the outer sheath and inner catheter, the user cannot easily monitor or attend to the positioning of the outer sheath in the hemostasis valve to ensure accurate stent placement, such that an assistant must be present to attend to the positioning of the outer sheath in the hemostasis valve and accurate positioning of the stent.

Other vascular stent placement delivery systems offer one-handed operation by converting hand-movements into indexed movement of the outer sheath. Such systems generally still operate, however, with a 1:1 ratio of handle movement to stent deployment distance. In other words, such systems do not provide mechanical advantage to accommodate, or reduce the amount of work required for, deployment of longer stents as compared to deployment of shorter stents.

BRIEF SUMMARY

In one aspect, a stent delivery system includes a wire collection device with a plurality of nested wire collection drums, a retraction wire, a thumbwheel, and a catching mechanism. The plurality of nested wire collection drums include a first drum concentric in a second drum. The inner diameter of the second drum is larger than the outer diameter of the first drum. The retraction wire is attached to the first drum and extends through a slot of the second drum. The thumbwheel is coupled to the first drum and can be rotated to actuate rotation of the first drum to collect the retraction wire around the diameter of the first drum. The retraction wire can be connected to a proximal end of an outer sheath of the stent delivery system. The catching mechanism can rotate about the first drum so as to engage a catch portion of the second drum to actuate rotation of the second drum. This collects the retraction wire around an outer diameter of the second drum, and increases the collection diameter of the retraction wire and provides a mechanical advantage for sheath retraction.

In another aspect, a method for collecting a retraction wire in a stent delivery system includes rotating a thumbwheel that is coupled to a plurality of nested wire collection drums. A first drum is concentric in a second drum. The inner diameter of the second drum is larger than a diameter of the inner drum. A slot in the second drum is configured to allow a retraction wire to pass through the second drum to the first drum. Rotating the thumbwheel actuates rotation of the inner drum and actuates rotation of a catching mechanism. Rotation of the inner drum collects the retraction wire around the diameter of the first drum. The retraction wire is coupled to a proximal end of an outer sheath of the stent delivery system. Collecting the retraction wire retracts the outer sheath to deploy a self-expanding stent. The catching mechanism can be rotated about the first until the catching mechanism engages a catch portion of the second drum, which actuates rotation of the second drum to collect the retraction wire around an outer diameter of the second drum. This increases the collection diameter of the retraction wire to provide a mechanical advantage.

In another aspect, a handle of a stent delivery system includes a wire collection device with a plurality of concentrically nested wire collection drums, a retraction wire, a thumbwheel, a first catching mechanism and a second catching mechanism. The plurality of concentrically nested wire collection drums includes an inner drum that is concentric in a first outer drum and a second outer drum. The inner diameter of the first outer drum is larger than the outer diameter of the inner drum. The inner diameter of the second outer drum is larger than the outer diameter of the first outer drum. The retraction wire is attached to the inner drum and extends through a slot of the second outer drum and a slot of the first outer drum. The thumbwheel is coupled to the inner drum. The thumbwheel can be rotated to actuate rotation of the inner drum to collect the retraction wire around the outer diameter of the inner drum. A distal end of the retraction wire is connected to a proximal end of an outer sheath of the stent delivery system. The first catching mechanism can be rotated about the inner drum and engage a catch portion of the first outer drum to actuate rotation of the first outer drum. The first outer drum can engage the retraction wire to cause the retraction wire to collect around the outer diameter of the first outer drum. This increases the collection diameter of the retraction wire to increase a mechanical advantage. The second catching mechanism can be rotated about the first outer drum and engage a catch portion of the second outer drum. This actuates rotation of the second drum until it engages the retraction wire, causing the retraction wire to collect around an outer diameter of the second collection drum. This further increases the collection diameter of the retraction wire to further increase the mechanical advantage.

DETAILED DESCRIPTION

Various embodiments are described below with reference to the drawings. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

A wire collection device for a stent delivery system and a method for collecting a retraction wire in a stent delivery system are provided in some embodiments. The stent delivery device includes a retraction wire that is attached, at a proximal end, to a wire collection device that is rotatable to pull and collect the retraction wire around a plurality of nested collection drums. The wire collection device includes a thumbwheel and a plurality of nested collection drums that increase the collection diameter of the retraction wire during stent deployment. A user may retract the outer sheath by turning the thumbwheel to pull and collect the retraction wire around the collection diameter.

A distal end of the retraction wire is connected or attached to a proximal end of an outer sheath that holds a stent at a distal end of an inner catheter. The inner catheter extends through the outer sheath from a proximal end near the wire collection device to a distal end near the stent. The stent and the distal ends of the inner catheter and outer sheath are inserted into a body vessel until the stent is located at a desired location. As the thumbwheel is turned, the wire collection device pulls and collects the retraction wire around the collection drums, thereby retracting the outer sheath across the inner catheter to uncover the stent while the internal catheter holds the stent in the desired location. The stent may be a self-expanding stent, or a stent that is expanded by the force of a balloon. In some embodiments, the diameter of the collection drums may be greater than the diameter of the thumbwheel, so that the wire collection device provides a mechanical advantage to the user. In other words, the wire collection device may provide a mechanical advantage that is greater than 1:1. As compared with a pin and pull system, the wire collection device may require less force from the user for stent deployment.

As used herein, "retraction wire" means a rope, cord, wire, cable, belt, chain, or any other strand(s) of material that is suitable for use in a stent deliver system to retract or pull an outer sheath to allow stent deployment or delivery. The term "nested collection drums," as used herein, means one or more axles, spindles, or other cylindrical structures that are concentric, or rotate about a common axis of rotation. The wire collection device may be used with one or more retraction wires, and may include one or more sets of nested collection drums. As used herein, "collection diameter" refers to the diameter around which a retraction wire collects, or is wound. Thus, the "collection diameter" may increase as the retraction wire overlaps itself as it is being collected, or wound, around an axle, spindle, collection drum, or other cylindrical structure. As used herein, numerical terms such as "first," "second," and "third," etc. does not refer to or limit any particular sequence, order, or configuration of components. Numerical terms may be used herein to describe various elements, components, regions, sections, and/or parameters, and/or to distinguish one element, component, region, section, and/or parameter from another.

When the wire collection device is used with a self-expanding stent, the required deployment force may be greater during initial deployment of the stent and may decrease as the outer sheath uncovers more of the stent. As used herein, "required deployment force" refers to an amount of force required to overcome the frictional forces between the outer sheath and the stent, frictional forces between the outer sheath and an inner catheter that holds the stent in place as the outer sheath is retracted, and frictional forces between the outer sheath and the surrounding body vessels where the stent is being implanted or placed.

The wire collection device may provide the user of the stent delivery system with a more consistent "touch and feel" by reducing the variation in amount of force required from the user to deploy the stent. This may be accomplished by increasing the mechanical advantage provided to the user as the required stent deployment force increases, or by decreasing the mechanical advantage as the required stent deployment force decreases, where the mechanical advantage of the wire collection device is determined by the ratio of the thumbwheel diameter to collection diameter. More particularly, the mechanical advantage increases as the collection diameter increases relative to the diameter of the thumbwheel, or the mechanical advantage decreases with each larger drum and approaches a 1:1 ratio. The plurality of nested collection drums may be sized and configured to control the degree and rate of change in the mechanical advantage provided during stent deployment. As the retraction wire collects around larger diameter drums, the stent deployment distance increases for the same amount of rotation of the thumbwheel. The number of drums may be changed to increase or decrease the number of increments for changing the collection diameter.

The wire collection device may provide a mechanical advantage such that the deployment distance, or retraction distance of the outer sheath, increases with hand movements of the user, or revolutions of the thumbwheel. The wire collection device controls retraction of the outer sheath so as to improve user feel and control for positioning the inner catheter. The wire collection device may be configured so that the user may exert a steady, or consistent force, throughout the deployment despite variation in the force required to retract the outer sheath, or deploy the stent. The wire collection device may provide a mechanical advantage to the user that results in a 1:1 ratio, or greater than or less than a 1:1 ratio, of handle movement to stent deployment distance.

Figure 1A:
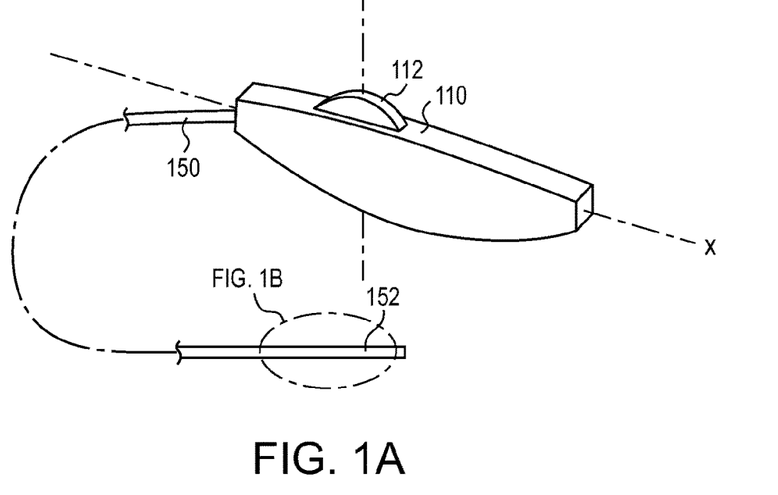
FIG. 1a is a view of an exemplary wire collection device for a stent delivery system.
Figure 1B:
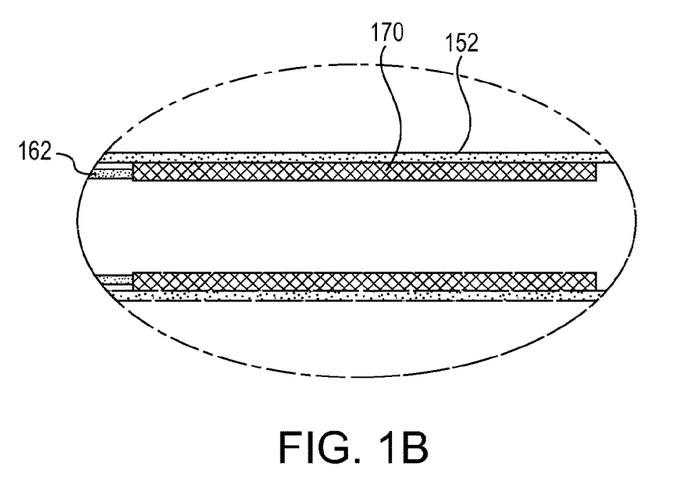
FIG. 1b is a detailed cross-sectional view of an exemplary wire collection device for a stent delivery system.
Figure 1C:
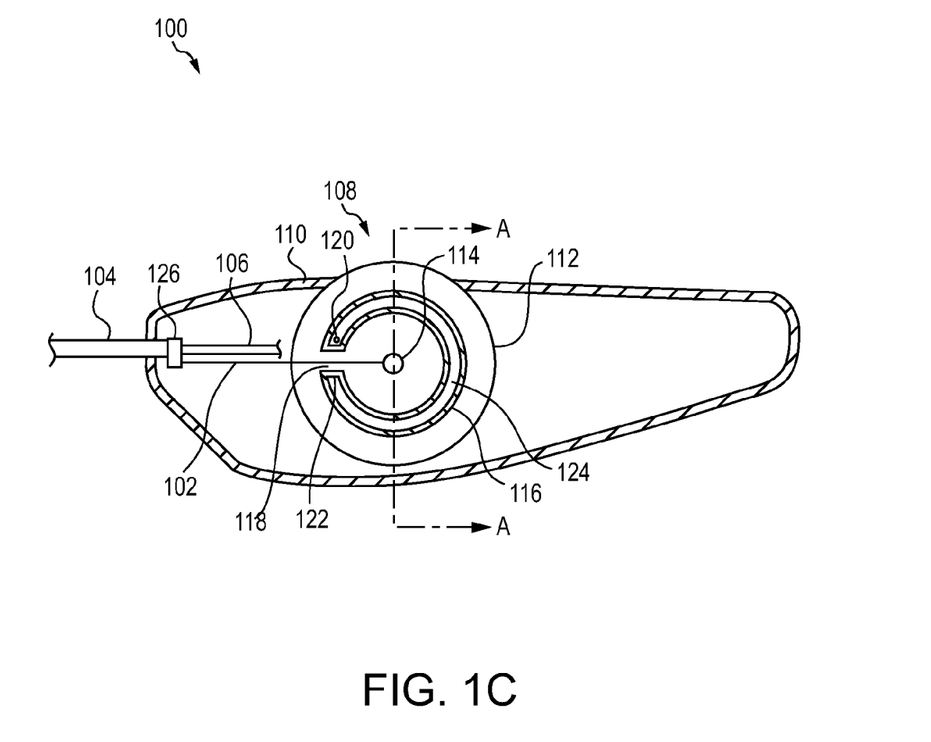
FIG. 1c is a longitudinal cross-sectional view of an exemplary wire collection device for a stent delivery system.
Figure 2:
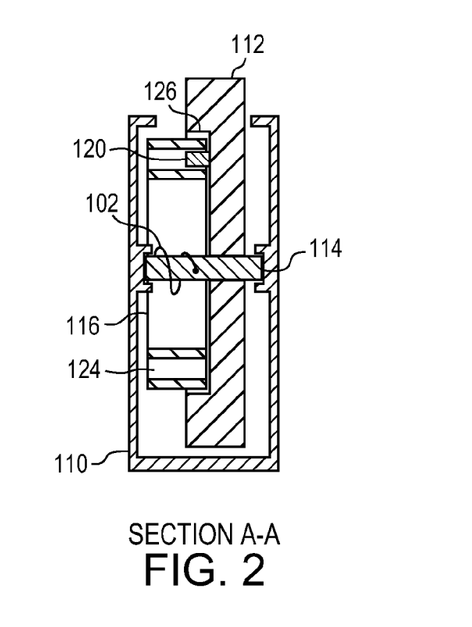
FIG. 2 is a transverse cross sectional view of an exemplary wire collection device for a stent delivery system.
Figure 3:
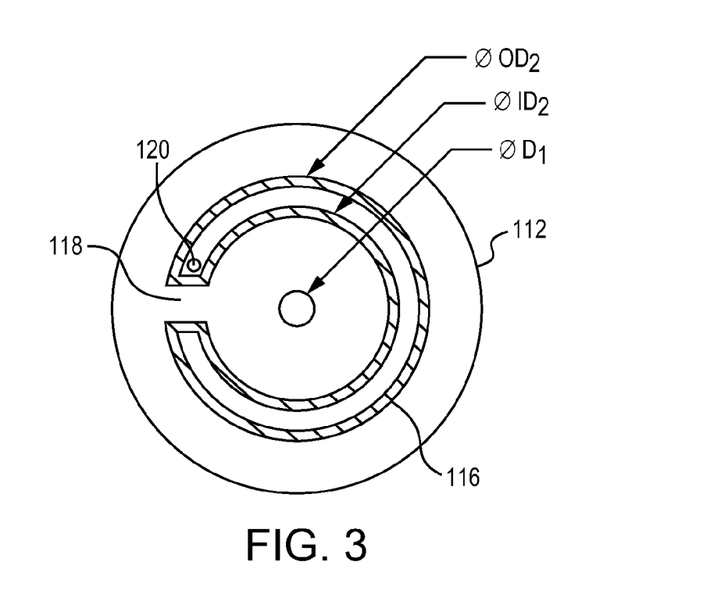
FIG. 3 is a partial view of a longitudinal cross-sectional view of an exemplary wire collection device for a stent delivery system that includes a transmission mechanism.

In some embodiments, as illustrated with reference to FIGS. 1-3, a stent delivery system 100 include a retraction wire 102 coupled to an outer sheath 104, an inner catheter 106 extending through the outer sheath 104, a wire collection device 108, and a handle 110 housing the wire collection device 108. The retraction wire 102 may be attached, directly or indirectly, to a proximal end 150 of the outer sheath 104 and at or near a proximal end 160 of the internal catheter 106. The wire collection device 108 includes a thumbwheel 112, an inner, or a first, collection drum 114, and at least one outer, or second, collection drum 116. As described below, the wire collection device may include any number of nested collection drums. The size and number of drums may be determined based on deployment force required for sheath retraction, distance of sheath retraction, desired speed of sheath retraction, and required degree of accuracy and precision in stent placement. The retraction wire 102 extends through a slot 118 of the second drum 116 and is attached to the first drum 114, so that when the first drum 114 rotates, the retraction wire 102 collects, or winds, around the diameter $D_1$ of the first drum 114 in the gap between the first drum 114 and the inner diameter $ID_2$ of the second drum 116. The slot 118 may give the second drum 116 a C-shaped profile partially or fully through the height of the drum 116. For example, the slot 118 may extend from one planar face of the drum halfway, or more or less, towards the opposite planar face of the drum to allow for the retraction wire 102 to pass through the second drum 116 to the first drum. Alternatively, the slot 118 may be a hole in a curved wall of the drum. The thumbwheel 112, the first drum 114, and the second drum 116, may be made of plastic, metal, ABS, polycarbonate, POM, PTFE, aluminum, glass-filled plastics, stainless steel or any combination thereof, or any other material that is sufficiently rigid to withstand the force required to turn the thumbwheel 112 and the required deployment force, and sufficiently lightweight for use in a surgical procedure.

Rotation of the thumbwheel 112 actuates rotation of the inner, or first, collection drum 114 to collect, or wind, the retraction wire 102 around, or about, the diameter $D_1$ of the first collection drum 114. As used herein, the term "actuates rotation" means to cause rotation, either directly or indirectly. Rotating, or turning, the thumbwheel 112 also rotates a catching mechanism 120 about the first drum 114, thereby causing the catching mechanism 120 to engage, or make contact, with a catch portion 122 of the second drum 116. When the catching mechanism 120 engages the catch portion 122, this in turn actuates rotation of the second drum 116 such that the slot 118 rotates and guides the retraction wire 102 to collect around the outer diameter $OD_2$ of the second drum 116. When the retraction wire 102 begins to collect around the outer diameter $OD_2$ of the second drum 116, the collection diameter of the retraction wire effectively increases, thereby increasing the mechanical advantage for sheath retraction.

The initial required deployment force, or the amount of force required to begin retraction of the outer sheath 104, depends on the force required to overcome the frictional force between the outer sheath 104 and the stent 170. The stent 170 may be located at or near a distal end 152 of the outer sheath 104 and a distal end 162 of the internal catheter 106. With reference to FIG. 1, at the truncated portion of the internal catheter 106, the proximal end 160 of the internal catheter 106 may be held in place by a known mechanism, structure, or attachment, by the housing of the handle 110. As the outer sheath 104 begins to move, or retract, the required deployment force, or force required to continue retracting the outer sheath, decreases. Thus, decreasing the mechanical advantage, as the required deployment force decreases, could reduce the variation in the amount of force required from the user. The wire collection device 108 decreases the mechanical advantage provided to the user as the collection diameter increases from the smaller diameter to a larger diameter, for example, from diameter $D_1$ of the first drum 114 to the diameter $OD_2$ of the second drum 116. Therefore, the ratio of movement of the thumbwheel 112 to stent deployment distance decreases as the collection diameter increases. This may provide the user with a more consistent "feel" throughout the deployment of the stent.

In some embodiments, the thumbwheel 112 may be aligned or concentric with the first drum 114 and the second drum 116. With reference to FIGS. 1 and 2, for example, the thumbwheel 112 is mounted on the first drum 114, and the catching mechanism 120 protrudes from, or is fixed to, the thumbwheel 112, and rotates about the axis of the first drum 112. As used herein, the term "rotates about" means to travel in a circular or substantially circular, or a repetitive path, around an object or an axis or to rotate about a shared axis together with the object at the same, or substantially the same, angular velocity. The catching mechanism 120 may be a pin, a tab, a knob, or other suitable structure for engaging the catching portion 122 of the second drum. As the thumbwheel 112 turns, the catching mechanism 120 travels along a channel 124 of the second drum 116 until it reaches the catching portion 122. The channel 124 may be a C-shaped groove having a depth that is at least the height of the catching mechanism 120. Alternatively, the channel 124 may be a cut-out that extends through the height of the second drum. The channel 124 may run along a portion or the entire length of the C-shaped profile of the second drum 116. The catching mechanism 120 may be initially located at one end of the channel 124, and rotate, or travel, along the channel 124 until the catching mechanism 120 engages the catching portion 122 at the other end of the channel 124.

When the catching mechanism 120 engages the catching portion 122, continued rotation of the thumbwheel 114 will actuate rotation of the second drum 116. In some embodiments, the second drum 116 is seated in a blind hole 126 in the thumbwheel 112. The blind hole 126 maintains the position of the second drum 116 as it rotates about the first drum 114. The first drum 114 may be an axle or a spindle on which the thumbwheel 112 is fixedly or rotatably mounted. The first drum 114 is supported by the housing of the handle 110, and may be rotatable or fixed in relation to the housing. The thumbwheel 112 may be notched or grooved to provide a surface that is easier to grip. An upper portion of the thumbwheel 112 may protrude from the housing of the handle 110 so as to allow the user to rotate the thumbwheel 112. In some embodiments, the wire collection device 108 may include a ratchet, or other clutch system, that allows the thumbwheel 112 to turn in only one direction, and/or prevents the thumbwheel 112 from moving when the user is not applying force to the thumbwheel 112.

In some embodiments, the retraction wire 102 is coupled to the outer sheath 104 by a sledge 126 that is within the housing of the handle 110. The inner sheath 106 extends through an aperture in the sledge 126. As the retraction wire 102 collects around the wire collection device 108, the outer sheath 106 and sledge 126 slide across the inner sheath 106, allowing the inner sheath 106 to maintain its position.

Figure 4:
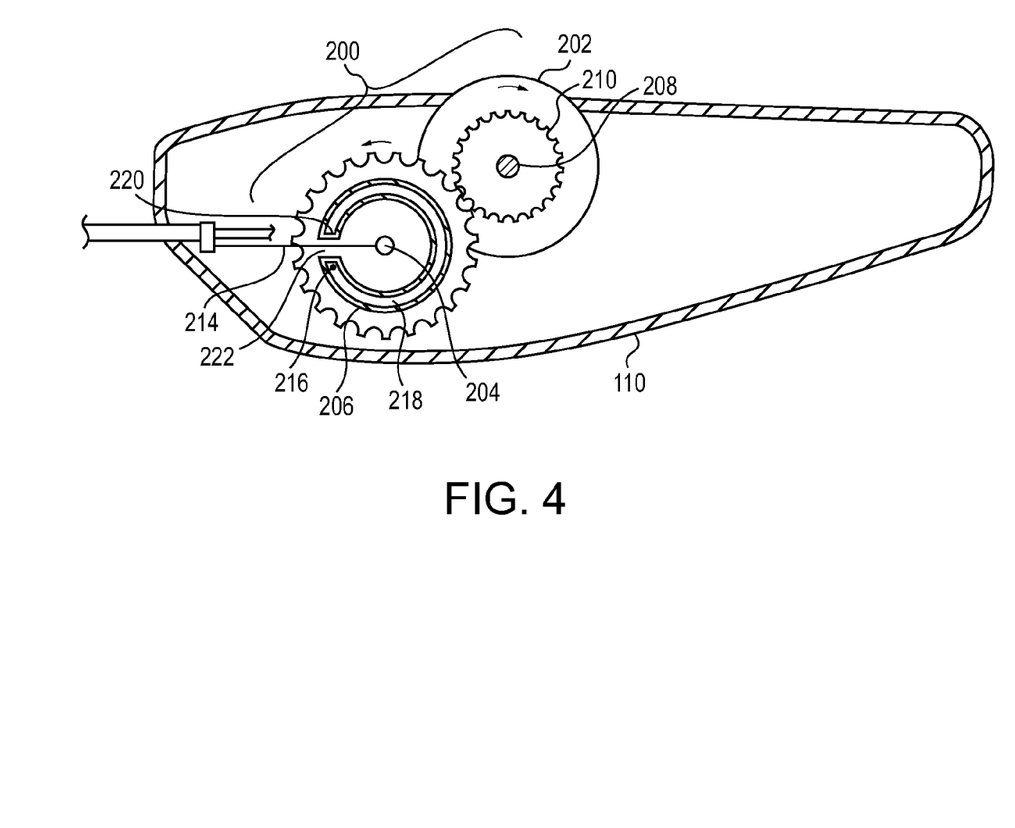
FIG. 4 is a longitudinal cross sectional view of an exemplary wire collection device for a stent delivery system.

In some embodiments, as illustrated with reference to FIG. 4, of a wire collection device 200 for a stent delivery system, the thumbwheel 202 may be offset from the nested wire collection drums, including the first collection drum 204 concentric in the second collection drum 206. For example, the thumbwheel 202 may be mounted on an axle 208 that is axially offset from the first collection drum 204. The thumbwheel 202 is coupled to the first drum 204, for example, by a transmission mechanism, such as mesh gears 210, 212. Mesh gear 210 may be formed or molded as part of the thumbwheel 202, or may be a separate component that is mounted on the axle 208. When the thumbwheel 202 rotates, gear 210 engages gear 212, thereby actuating rotation of the first drum 204 to collect the retraction wire 214 around the diameter of the first drum 204. Rotation of the thumbwheel 204 may also rotate the catching mechanism 216 about the first drum 204. As in embodiments of the wire collection device 108 shown in FIGS. 1-3, the second drum 206 may include a channel 218. The catching mechanism 216 may travel along the channel 218 as the thumbwheel 202 rotates the gears 210, 212. When the catching mechanism 216 engages the catch portion 220, this actuates rotation of the second drum 206 so that slot 222 rotates and guides the retraction wire 214 to collect around the outer diameter of the second drum 206. In other embodiments, the transmission mechanism may include a transmission belt, a rack and pinion, a clutch, a ratchet, or any combination thereof.

Figure 5:
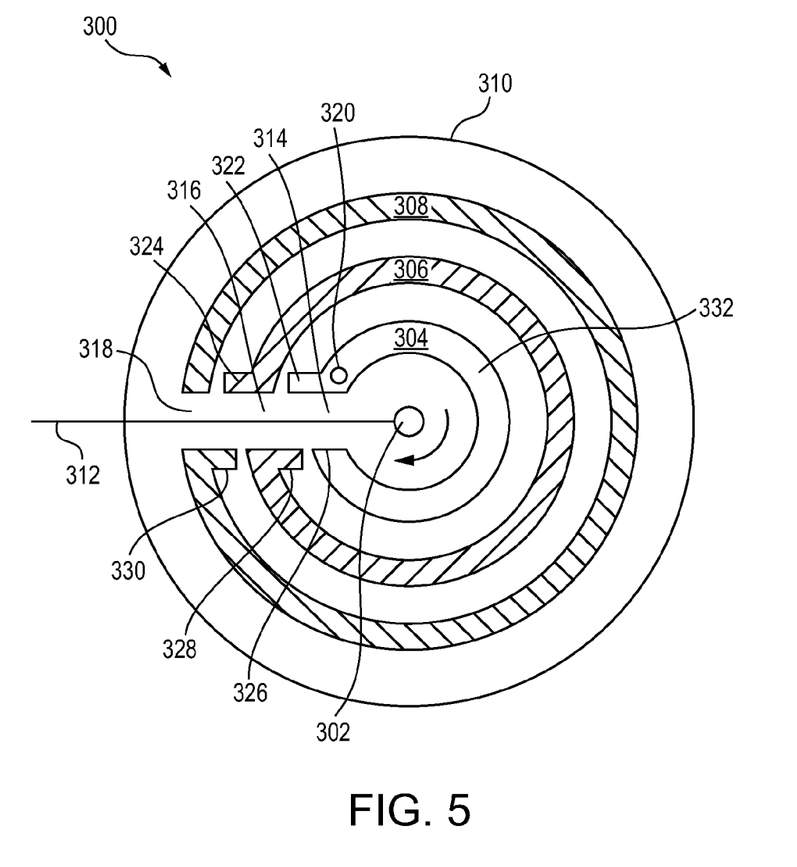
FIG. 5 is a longitudinal cross sectional view of an exemplary wire collection device for a stent delivery system.

In some embodiments, as illustrated with reference to FIGS. 5 and 6, a wire collection device 300 may include a plurality of nested wire collection drums, including a first drum 302, a second drum 304, a third drum 306, and a fourth drum 308, all concentrically arranged. The thumbwheel 310 may be concentric, or co-axial, with the nested wire collection drums 302, 304, 306, 308. Alternatively, the thumbwheel 310 may be co-axially offset from the nested wire collection drums 302, 304, 306, 308, and coupled to the first collection drum 302 by a transmission mechanism. The transmission mechanism may include mesh gears, a transmission belt, a rack and pinion, a clutch, a ratchet, or any combination thereof. A retraction wire 312 extends through slots 314, 316, 318 of the second, third, and fourth drums 304, 306, 308. The retraction wire 312 is attached to the first drum, such that rotation of the thumbwheel 310 actuates rotation of the first drum 302 to collect the retraction wire around the diameter of the first drum 302. The wire collection device 300 also includes catching mechanisms 320, 322, 324, and corresponding catch portions 326, 328, 330.

In operation, the first catching mechanism 320 rotates with the thumbwheel 310. Alternatively, the first catching mechanism 320 may be configured to begin rotation after a predetermined length of the retraction wire 312 has been collected around the first drum 302. The first catching mechanism 320 may be a pin that travels along a channel 332 in the second drum 304 and engages the catch portion 326 of the second drum 304. Continued rotation of the thumbwheel 310 actuates rotation of the second drum 304 together with the first drum 302. The catch portion 328 of the second drum 304 may be an inner surface of the channel 332. As the second drum 304 rotates, the slot 314 of the second drum 304 guides the retraction wire 312 to collect around the outer diameter of the second drum 304, thereby increasing the collection diameter of the retraction wire 312.

The second drum 304 continues to rotate until the second catching mechanism 322 engages the second catch portion 328, thereby, actuating rotation of the third drum 306, along with the first and second drums 302, 304. The second catching mechanism 322 may be a tab that protrudes, or extends, from the outer diameter of the first drum 302 towards the second drum 304. The second catch portion 328 may be a tab protruding, or extending, from the inner diameter of the third drum 306 towards the second drum 304. As the third drum 306 rotates, the slot 316 of the third drum 306 guides the retraction wire 312 to collect around the outer diameter of the third drum 306, thereby further increasing the collection diameter of the retraction wire 312.

Continued rotation of the thumbwheel 310 causes the third catching mechanism 324 to rotate about the first drum 302 until the third catching mechanism 324 engages the third catch portion 330 on the fourth drum 308. This actuates rotation of the fourth drum 308, along with the first, second, and third drums 302, 304, 306. The third catching mechanism 324 may be a tab that extends from the outer diameter of the third drum 306 towards the fourth drum 308. The third catch portion 330 may be a tab that extends from the inner diameter of the fourth drum 308 towards the third drum 306. As the fourth drum 308 rotates, the slot 318 of the fourth drum guides the retraction wire 312 to collect around the outer diameter of the fourth drum 308, thereby further increasing the collection diameter of the retraction wire 312.

Figure 6:
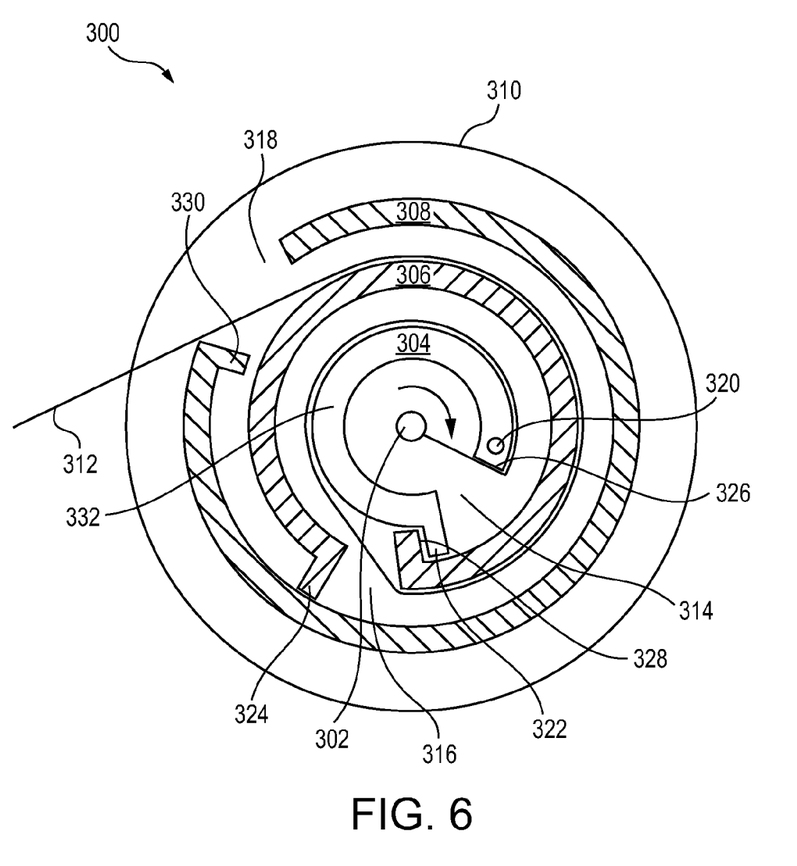
FIG. 6 is another longitudinal cross sectional view of an exemplary wire collection device for a stent delivery system.
Figure 7:
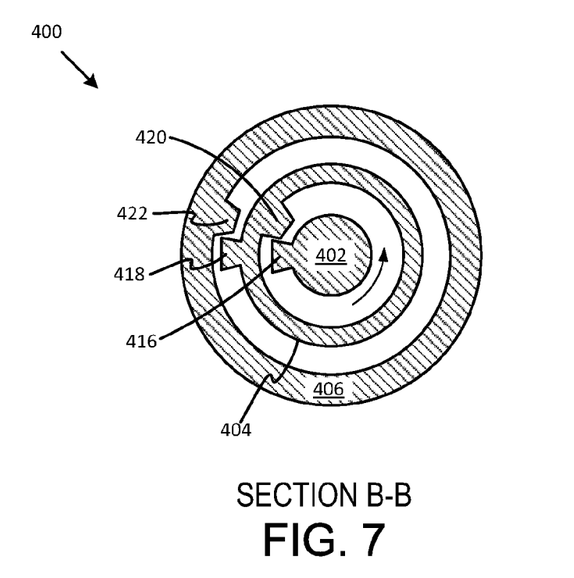
FIG. 7 is a cross sectional top view of an exemplary wire collection device for a stent delivery system.

With reference to FIG. 6, for example, with each full rotation of the thumbwheel 310, the collection diameter of the retraction wire 312 increases as the catching mechanisms 320, 322, 324 engage the catch portions 326, 328, 330 to actuate rotation of additional outer collection drums 304, 306, 308.

In some embodiments, as illustrated with reference to FIGS. 7-10, the wire collection device 400 may include nested collection drums, including a first, second, and third drum 402, 404, 406, concentrically seated. The thumbwheel 408 may be mounted on an end of the first drum 402, or may be machined or formed as a unitary piece with the first drum 402. Alternatively, the thumbwheel 408 may be co-axially offset from the nested collection drums 402, 404, 406, and coupled to the first drum 402 by a transmission mechanism. The transmission mechanism may include mesh gears, a transmission belt, a rack and pinion, a clutch, a ratchet, or any combination thereof. A retraction wire 410 extends through slots 412, 414 in the second and third drums 404, 406, and is attached to the first drum 402. Rotation of the thumbwheel 408 actuates rotation of the first drum 402 to collect the retraction wire 408 around the diameter of the first drum 402. The wire collection device 400 also includes catching mechanisms 416, 418, and corresponding catch portions 420, 422.

In operation, the first catching mechanism 414 rotates with the thumbwheel 408. Alternatively, in some embodiments, the first catching mechanism 416 may be configured to begin rotation after a predetermined length of the retraction wire 410 has been collected around the first drum 402. The first catching mechanism 416 may be a tab that protrudes from the diameter of the first drum 402 towards the second drum 404. As the first drum 402 rotates, the first catching mechanism 416 rotates with, or about, the first drum 402, until the catching mechanism 416 engages the first catch portion 420. The first catch portion 420 may be a tab protruding from the inner diameter of the second drum 404 towards the first drum 402. Continued rotation of the thumbwheel 408 actuates rotation of the second drum 404 together with the first drum 402. As the second drum 404 rotates, the slot 412 of the second drum 404 guides the retraction wire 410 to collect around the outer diameter of the second drum 404, thereby increasing the collection diameter of the retraction wire 410.

The second drum 404 continues to rotate until the second catching mechanism 418 engages the second catch portion 422, thereby actuating rotation of the third drum 406. The second catching mechanism 418 may be a tab that protrudes, or extends, from the outer diameter of the second drum 404 towards the third drum 406. The second catch portion 422 may be a tab that protrudes or extends, from the inner diameter of the third drum 406 towards the second drum 404. As the third drum 406 rotates, the slot 414 of the third drum guides the retraction wire 410 to collect around the outer diameter of the second drum 404, thereby further increasing the diameter of the retraction wire 410.

Figure 8:
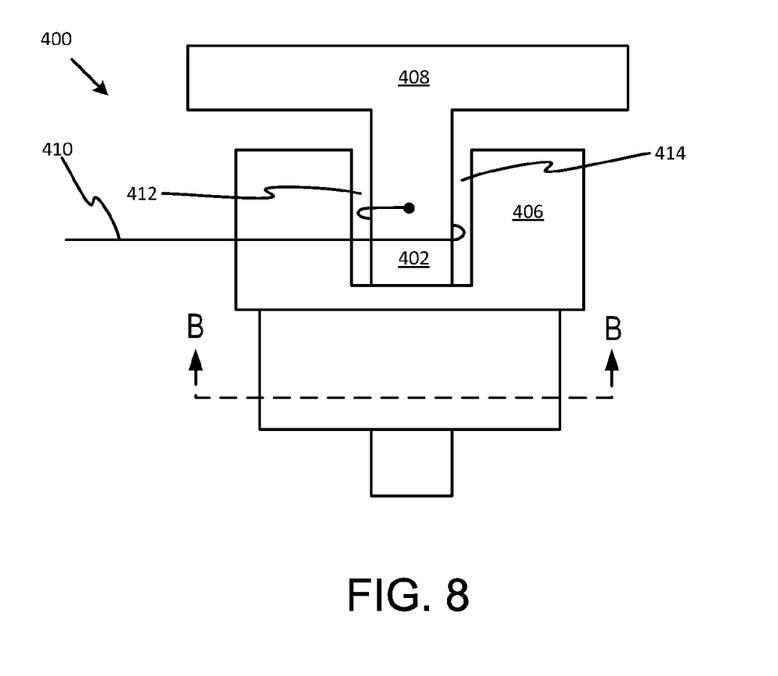
FIG. 8 is a side view of an exemplary wire collection device for a stent delivery system.
Figure 9:
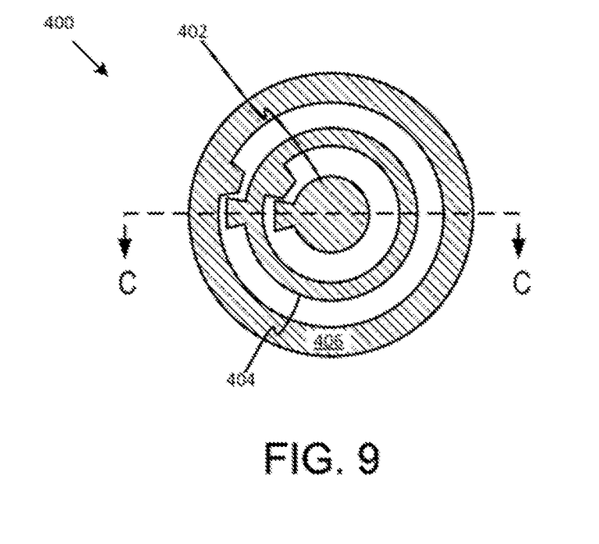
FIG. 9 is a cross sectional top view of an exemplary wire collection device for a stent delivery system.
Figure 10:
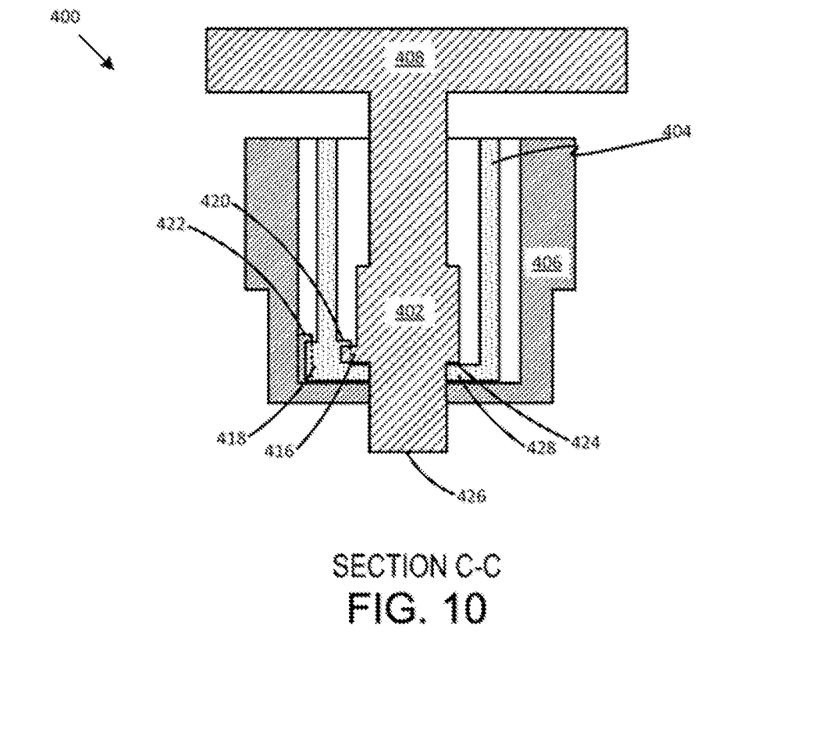
FIG. 10 is a cross sectional side view of an exemplary wire collection device for a stent delivery system.

In some embodiments, as illustrated with reference to FIGS. 8 and 10, for example, the wire collection device 400 may include collection drums that are seated partially or fully within other drums. The first drum 402 may be attached to, or formed as a part of, the thumbwheel 408. The first drum 402 has a lip 416 that runs partially or fully around the diameter nearer a free end 426 of the first drum 402. The diameter of the first drum 402 may vary to provide a sufficient gap between the first drum 402 and the second drum 404 to allow the retraction wire 410 to collect between the first drum 402 and the second drum 404. The first catching mechanism may be a tab nearer the free end 426 of the first drum 402. The free end 426 of the first drum 402 is seated in, or extends through, a hole in a bottom portion 428 of the second drum 404. As used herein, the term "bottom" means a portion of the collection drum that is at or near a surface of the drum, and does not limited to the use of the wire collection device to any particular orientation. For example, the "bottom portion" of a drum may be a portion that is on a left or right side when viewing the wire collection device.

The catch portion 420 may be a tab or protrusion on the inner surface of the second drum 404 that is configured (e.g., sized, positioned) to allow a predetermined amount of rotation of the first drum 402, or a predetermined length of the retraction wire 410 to collect around the first drum 402, before the catching mechanism 416 meets the catch portion 420. Similarly, the catch portion 422 may be a tab or protrusion on the inner surface of the third drum 406 that is configured (e.g., sized, positioned) to allow a predetermined amount of rotation of the second drum 404, or a predetermined length of the retraction wire 410 to collect around the second drum 404, before the catching mechanism 418 meets the catch portion 422.

The diameters of the drums 402, 404, 406 and the locations of the catching mechanisms 416, 418 and corresponding catch portions 420, 422 are determined based on the length of the stent, or the distance that the outer sheath must be retracted to deploy the stent, and the variation in deployment force during sheath retraction. The thickness (e.g., diameter of the inner drum, or first drum, and distance between the inner and outer diameters of outer drums) of the drums 402, 404, 403 may depend on the strength of the material used for the drums, diameter of the retraction wire 410, or space required to collect the retraction wire 410, and the force to be applied.

Figure 11:
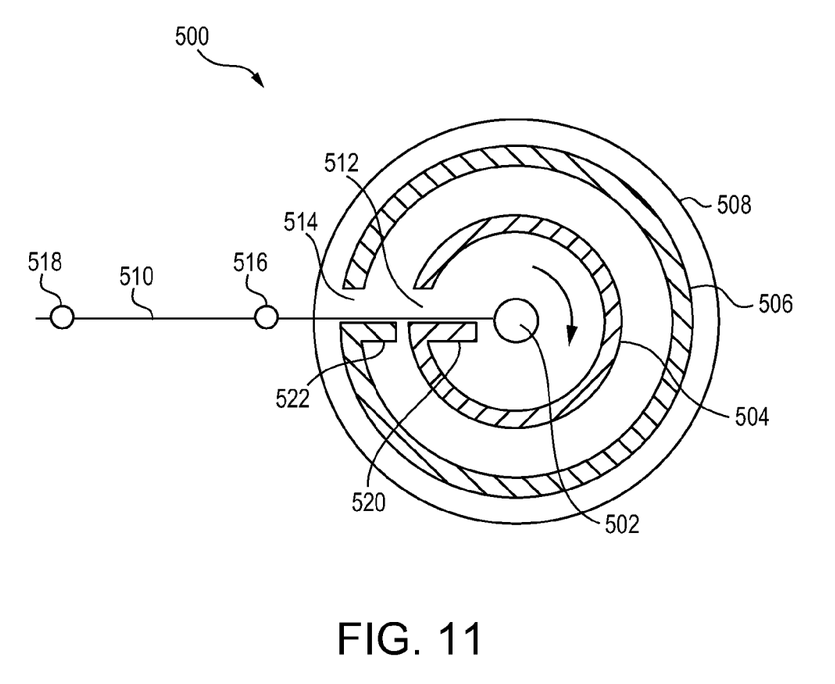
FIG. 11 is a longitudinal cross sectional view of an exemplary wire collection device for a stent delivery system.
Figure 12:
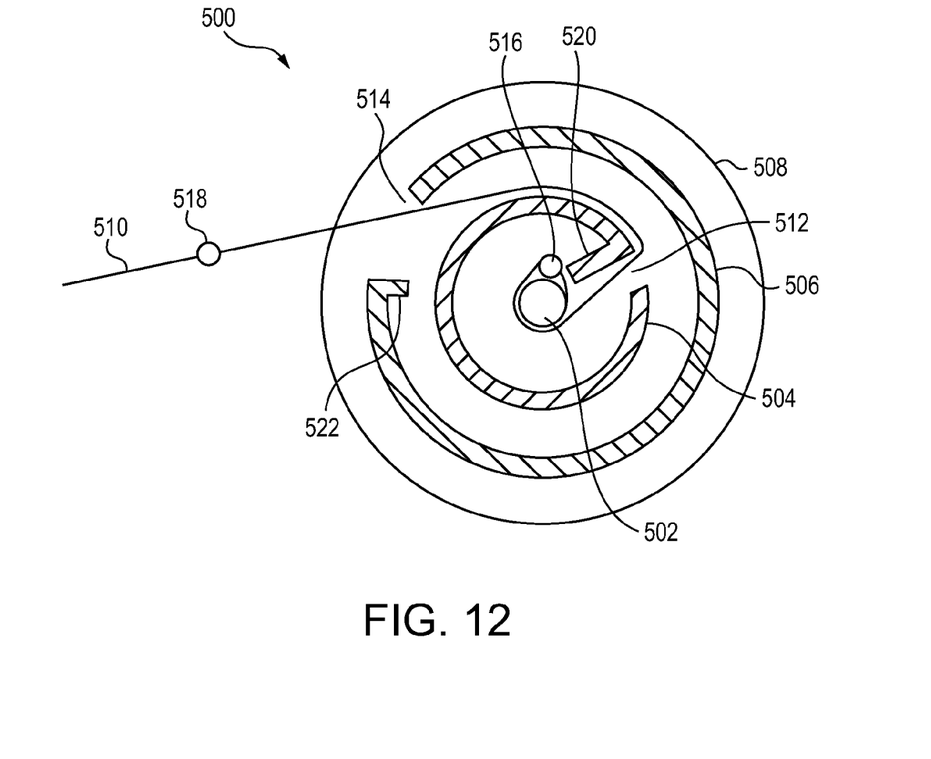
FIG. 12 is another longitudinal cross sectional view of an exemplary wire collection device for a stent delivery system.

In some embodiments, as illustrated with reference to FIGS. 11 and 12, the wire collection device 500 may include nested collection drums, including first, second, and third drums 502, 504, 506. The thumbwheel 508 may be co-axially coupled to the first drum 502. For example, the thumbwheel 508 may be mounted on an end of the first drum 502, or may be machined or formed as a unitary piece with the first drum 502. Alternatively, the thumbwheel 508 may be mounted on an independent axle that is co-axially offset from the nested collection drums 502, 504, 506, and coupled to the first drum 502 by a transmission mechanism. The transmission mechanism may include mesh gears, a transmission belt, a rack and pinion, a clutch, a ratchet, or any combination thereof. A retraction wire 510 is attached to the first drum 502, and extends through slots 512, 514 of the second and third drums 504, 506 to the first drum 502. Catching mechanisms 516, 518 are located along the retraction wire 510.

In operation, rotation of the thumbwheel 508 actuates rotation of the first drum 502 to collect the retraction wire 510 around the diameter of the first drum 502. As the retraction wire 510 collects around the first drum 502, the first catching mechanism 516 passes through the slots 512, 514, and is pulled around, or rotates about, the first drum 502 as the second and third drums 504, 506 remain in position (e.g., does not substantially rotate). Continued rotation of the thumbwheel 508 causes the catching mechanism 516 to engage, or meet, a catch portion 520, thereby actuating rotation of the second drum 504. The catch portion 520 may be a tab, or any other structure or attachment, that protrudes, or extends from, the inner diameter of the second drum 504 towards the inner, or first, drum 502. As the second drum 504 rotates the slot 512 guides the retraction wire 510 around the outer diameter of the second drum 504, thereby increasing the collection diameter of the retraction wire 510. Continued rotation of the thumbwheel 508 rotates the second drum 504 until the second catching mechanism 518 passes through slot 514, and is pulled around, or rotates about, the first drum 502 and the second drum 504. The third drum 506 remains in position until the second catching mechanism 518 engages, or meets, the second catch portion 522, thereby actuating rotation of the third drum 506. As the third drum 506 rotates, the slot 514 guides the retraction wire 510 around the outer diameter of the third drum 506, thereby further increasing the collection diameter of the retraction wire 510.

The catching mechanisms 516, 518 may be a bead, a link, or any other structure that is configured (e.g., sized, shaped, and/or located) to pass through the slots 512, 514, and make contact with the catch portions 520, 522, and to allow and actuate rotation of the outer drums 504, 506. The location of the catching mechanisms 516, 518 along the retraction wire 510, or the distance between the catching mechanisms 516, 518 may depend on the desired amount of sheath retraction before increasing the collection diameter of the retraction wire 510. The distance between the catching mechanisms 516, 518 may be configured so that the retraction wire 510 collects around the outer diameter of the first and/or second drum 502, 504 for multiple full rotations before increasing the collection diameter. The catching portions 520, 522 are configured to allow the catching mechanisms 516, 518 to engage the catch portions 520, 522 while providing sufficient clearance to allow the retraction wire 510 to pass between the catching mechanisms 516, 518 and the first and second drums 502, 504, respectively.

In some embodiments, for example embodiments 108, 200, 300, 400, 500 shown in FIGS. 1-12, the wire collection device may include any number of collection drums. The drums may be generally cylindrical, or may be shaped as cams, to vary the collection diameter as a drum rotates. The size and number of drums may be determined based on deployment force required for sheath retraction, distance of sheath retraction, desired speed of sheath retraction, and required degree of accuracy and precision in stent placement. The catching mechanisms and catch portions may vary in size, shape, location, and placement along the drums or the retraction wire may also be based on deployment force required for sheath retraction, distance of sheath retraction, desired speed of sheath retraction, and required degree of accuracy and precision in stent placement. For example, the catching mechanisms and catch portions may be located at edges or ends of the drums, or may be located midway between ends or edges. The drums may include holes, counterbores, lips, and other structures to maintain position of the drums while they rotate.

Although various embodiments of the invention have been described, it will be apparent to those of ordinary skill in the art that many more embodiments and implementations are possible that are within the scope of the invention. For instance, steps of a method as displayed in the figures or reflected in the claims do not require a specific order of execution by way they are presented, unless specified. The disclosed steps are listed as exemplary such that additional or different steps may be executed or the steps may be executed in a different order. Those of skill in the art will appreciate that embodiments not expressly illustrated herein may be practiced within the scope of the claims, including that features described herein for different embodiments may be combined with each other and/or with currently-known or future-developed technologies while remaining within the scope of the claims.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. A wire collection device for a stent delivery system, the wire collection device comprising:
   a plurality of nested wire collection drums comprising a first drum concentric in at least one second drum, the at least one second drum comprising an inner diameter larger than an outer diameter of the first drum;
   a retraction wire attached to the first drum and extending through a slot of the at least one second drum;
   a thumbwheel coupled to the first drum and rotatable to actuate rotation of the first drum to collect the retraction wire around the outer diameter of the first drum, the retraction wire connected to a proximal end of an outer sheath of the stent delivery system; and
   a catching mechanism rotatable about the first drum so as to engage a catch portion of the at least one second drum to actuate rotation of the at least one second drum to collect the retraction wire around an outer diameter of the at least one second drum, thereby increasing a collection diameter of the retraction wire to provide a mechanical advantage for sheath retraction.

2. The wire collection device of claim 1, wherein the thumbwheel is concentric with the plurality of nested wire collection drums.

3. The wire collection device of claim 1, wherein the thumbwheel is offset from the plurality of nested wire collection drums and coupled to the first drum by a transmission mechanism comprising mesh gears, a belt, a rack and pinion, a clutch, a ratchet, or any combination thereof.

4. The wire collection device of claim 1, wherein:
   the catching mechanism comprises a tab protruding from the first drum towards the at least one second drum; and
   the catch portion comprises a tab protruding from the inner diameter of the at least one second drum towards the first drum.

5. The wire collection device of claim 1, wherein:
   the catching mechanism comprises a bead located along the retraction wire; and
   the catch portion comprises a tab protruding from the inner diameter of the at least one second drum towards the first drum.

6. The wire collection device of claim 1, wherein:
   the catching mechanism comprises a pin coupled to the thumbwheel;
   the thumbwheel is rotatable to cause the pin to travel along a channel of the at least one second drum until the pin engages the catch portion of the at least one second drum; and
   the catch portion of the at least one second drum comprises an inner surface of the channel of the at least one second drum.

7. The wire collection device of claim 6, wherein:

the plurality of nested wire collection drums further comprises at least a third drum concentric with the first drum and the at least one second drum, the at least one third drum comprising:

an inner diameter larger than the outer diameter of the at least one second drum; and a tab extending from an inner diameter of the third drum towards the at least one second drum;

the retraction wire extends through a slot of the third drum to the at least one second drum; and the at least one second drum further comprises a tab extending from the outer diameter of the at least one second drum towards the third drum, and the at least one second drum is rotatable such that the tab of the at least one second drum engages the tab of the third drum to actuate rotation of the at least one third drum to collect the retraction wire around an outer diameter of the second collection drum, thereby further increasing the collection diameter of the retraction wire to vary the mechanical advantage.

8. A wire collection device for a handle of a stent delivery system, the wire collection device comprising:

a plurality of concentrically nested wire collection drums comprising an inner drum concentric in a first outer drum and at least one second outer drum, the first outer drum comprising an inner diameter larger than an outer diameter of the inner drum and the at least one second outer drum comprising an inner diameter larger than an outer diameter of the first outer drum;

a retraction wire attached to the inner drum and extending through a slot of the at least one second outer drum and a slot of the first outer drum to the inner drum;

a thumbwheel coupled to the inner drum and rotatable to actuate rotation of the inner drum to collect the retraction wire around the outer diameter of the inner drum, a distal end of the retraction wire connected to a proximal end of an outer sheath of the stent delivery system; and a first catching mechanism rotatable about the inner drum so as to engage a catch portion of the first outer drum to actuate rotation of the first outer drum until the first outer drum engages the retraction wire causing the retraction wire to collect around the outer diameter of the first outer drum, thereby increasing a collection diameter of the retraction wire to vary a mechanical advantage;

a second catching mechanism rotatable about the first outer drum so as to engage a catch portion of the at least one second outer drum to actuate rotation of the at least one second outer drum until the at least one second outer drum engages the retraction wire causing the retraction wire to collect around an outer diameter of the second collection drum, thereby further increasing the collection diameter of the retraction wire to further vary the mechanical advantage.

9. The wire collection device of claim 8, wherein the thumbwheel is concentric in the plurality of nested wire collection drums.

10. The wire collection device of claim 8, wherein the thumbwheel is offset from the plurality of nested wire collection drums and coupled to the inner drum by a transmission mechanism comprising a belt, a rack and pinion, a clutch, a ratchet, or any combination thereof.

11. The wire collection device of claim 8, wherein:

the first catching mechanism comprises a first bead located along the retraction wire; and the catch portion of the first outer drum comprises a tab protruding from the inner diameter of the first outer drum towards the inner drum;

the second catching mechanism comprises a second bead located along the retraction wire at a predetermined distance from the first bead, the predetermined distance being at least a distance equal to a circumference of the inner drum; and the catch portion of the at least one second outer drum comprises a tab protruding from the inner diameter of the at least one second outer drum towards the first outer drum.

12. The wire collection device of claim 8, wherein:

the first catching mechanism comprises a pin coupled to the thumbwheel; and the inner drum is rotatable to cause the pin to travel along a channel of the first outer drum until the pin engages the catch portion of the first outer drum.

13. The wire collection device of claim 12, wherein:

the second catching mechanism comprises a tab protruding from the outer diameter of the first outer drum towards the at least one second outer drum; and the catch portion of the at least one second outer drum comprises a tab protruding from the inner diameter of the at least one second outer drum towards the first outer drum.

* * * * *